(12) United States Patent
Corthesy-Theulaz et al.

(10) Patent No.: US 8,021,656 B2
(45) Date of Patent: *Sep. 20, 2011

(54) PROBIOTICS FOR GUT NEUROMUSCULAR FUNCTIONS

(75) Inventors: Irène Corthesy-Theulaz, Epalinges (CH); Elena Verdu de Bercik, Ancaster (CA); Premysl Bercik, Ancaster (CA); Stephen Michael Collins, Dundas (CA)

(73) Assignee: Nestec S.A., Vevey (CH)

( * ) Notice: Subject to any disclaimer, the term of this patent is extended or adjusted under 35 U.S.C. 154(b) by 1342 days.

This patent is subject to a terminal disclaimer.

(21) Appl. No.: 10/522,295

(22) PCT Filed: Jul. 23, 2003

(86) PCT No.: PCT/EP03/08076

§ 371 (c)(1), (2), (4) Date: Jun. 16, 2006

(87) PCT Pub. No.: WO2004/009103

PCT Pub. Date: Jan. 29, 2004

(65) Prior Publication Data

US 2007/0128178 A1   Jun. 7, 2007

(30) Foreign Application Priority Data

Jul. 23, 2002 (EP) .................................. 02078064

(51) Int. Cl.
*A61K 35/74* (2006.01)
(52) U.S. Cl. ................................... 424/93.45
(58) Field of Classification Search .......... None
See application file for complete search history.

(56) References Cited

U.S. PATENT DOCUMENTS

| | | | |
|---|---|---|---|
| 6,805,852 B2 * | 10/2004 | Lin et al. ........................ | 424/1.11 |
| 6,835,376 B1 * | 12/2004 | Neeser et al. ................. | 424/93.45 |
| 6,887,465 B1 * | 5/2005 | Reniero et al. ................ | 424/93.45 |
| 7,029,669 B1 * | 4/2006 | Reniero et al. ................ | 424/93.45 |
| 7,678,370 B2 * | 3/2010 | Schiffrin et al. .............. | 424/93.45 |
| 2003/0031625 A1 * | 2/2003 | Lin et al. ........................ | 424/1.11 |
| 2003/0113306 A1 * | 6/2003 | Collins et al. ................. | 424/93.45 |
| 2004/0115308 A1 * | 6/2004 | Bengtsson-Riveros et al. ................................ | 426/61 |
| 2004/0208863 A1 * | 10/2004 | Versalovic et al. ............ | 424/115 |

FOREIGN PATENT DOCUMENTS

| WO | WO 97/00078 | 1/1997 |
|---|---|---|
| WO | 99/17788 | 4/1999 |
| WO | WO 01/11015 | 2/2001 |
| WO | WO 01/52667 | 7/2001 |
| WO | WO 01/97821 | 12/2001 |
| WO | WO 02/36137 | 5/2002 |

OTHER PUBLICATIONS

The Merck Manual, 17th edition (1999), pp. 312-313.*
Talley et al., Gut, 31(1), (Jan. 1990) 54-58 (Abstract).*
Sydow et al., Anathesiol. Intensivmed. Notfallmed. Schmerzther., 28(4), (Jun. 1993): 25860 (Abstract).*
Niedzielin et al. entitled "New possibility in the treatment of irritable bowel syndrome: probiotics as a modification of the flora of the colon" Gastroenterology 1998; 114: A402.
Thompson article entitled "Probiotics for irritable bowel syndrome: a light in the darkness?" *European Journal of Gastroenterology & Hepatology* 2001, vol. 13, No. 10, pp. 1135-1136.
Niedzielin et al. article entitled "A controlled, double-blind, randomized study on the efficacy of *Lactobacillus plantarum* 299V in patients with irritable bowel syndrome" *European Journal of Gastroenterlogy & Hepatology* 2001, vol. 13, No. 10, pp. 1143-1147.
O'Sullivan et al. article entitled "Bacterial supplementation in the irritable bowel syndrome. A randomized double-blind placebo-controlled crossover study" *Digest Liver Dis* 2000; vol. 32, pp. 294-301.
Madsen et al. article entitled "*Lactobacillus* Species Prevents Colitis in Interleukin 10 Gene-Deficient Mice" *Gastroenterology* vol. 116, No. 5, pp. 1107-1114, (1999).
Pochard et al. article entitled "Lactic acid bacteria inhibit $T_H2$ cytokine production by mononuclear cells from allergic patients" *J Allergy Clin Immunol* Oct. 2002, pp. 617-623.
Shida et al. article entitled "*Lactobacillus casei* Inhibits Antigen-Induced IgE Secretion through Regulation of Cytokine Production in Murine Splenocyte Cultures" *Int Arch Allergy Immunol* 1998, vol. 115, pp. 278-287.
Wallace et al. article entitled "Interactions of Lactic Acid Bacteria with Human Intestinal Epithelial Cells: Effects on Cytokine Production" *Journal of Food Protection* vol. 66, No. 3, 2003, pp, 466-472.
Holma et al. article entitled "Effects of *Lactobacillus rhamnosus* GG and *Lactobacillus reuteri* R2LC on Acetic Acid-induced Colitis in Rats" *Scand J Gastroenterol* 2001, vol. 6, pp. 630-635.
"Antitumorigenic activity of the prebiotic inulin enriched with oligofructose in combination with the probiotics *Lactobacillus rhamnosus* and *Bifidobacterium lactic* on azoxymethane-induced colon carcinogenesis in rats." Femla et al., Carcinogenesis, (23), (Nov. 2002) pp. 1953-1960.
"Effect of *Saccharomyces bouiardii* on cAMP- and Ca2+-dependent Cl-secretion in T84 cells." Czerucka et al., Dig. Dis. & Sciences, (Nov. 1999) pp. 2359-2368.
"Variable response to probiotics in two models of experimental colitis in rats." Shibolet et al., Inflam. Bowel Dis., (8), (Nov. 2002), pp. 399-406.
"Reduction of candidiasis by administering a probiotic composition." Balish et al., WO 99/17788 (1999) (Abstract).

* cited by examiner

*Primary Examiner* — Phyllis G. Spivack
(74) *Attorney, Agent, or Firm* — K&L Gates LLP

(57) ABSTRACT

The present invention relates to a method of treating gut pain or gut discomfort related or linked to gut muscular abnormalities comprising the step of administering to a human or an animal having gut pain or gut discomfort an effective amount of a selected probiotic.

5 Claims, 4 Drawing Sheets

SEQUENCE LISTING

```
<160> NUMBER OF SEQ ID NOS: 6

<210> SEQ ID NO 1
<211> LENGTH: 25
<212> TYPE: DNA
<213> ORGANISM: Homo sapiens

<400> SEQUENCE: 1
gttggataca ggccagactt tgttg                                     25

<210> SEQ ID NO 2
<211> LENGTH: 25
<212> TYPE: DNA
<213> ORGANISM: Homo sapiens

<400> SEQUENCE: 2
gattcaactt gcgctcatct taggc                                     25

<210> SEQ ID NO 3
<211> LENGTH: 20
<212> TYPE: DNA
<213> ORGANISM: Homo sapiens

<400> SEQUENCE: 3
tcacccgcgt gcctaatggt                                           20

<210> SEQ ID NO 4
<211> LENGTH: 20
<212> TYPE: DNA
<213> ORGANISM: Homo sapiens

<400> SEQUENCE: 4
ggagctgaag caatagttgg                                           20

<210> SEQ ID NO 5
<211> LENGTH: 20
<212> TYPE: DNA
<213> ORGANISM: Homo sapiens

<400> SEQUENCE: 5
tggtgccggg tctgatgatg                                           20

<210> SEQ ID NO 6
<211> LENGTH: 20
<212> TYPE: DNA
<213> ORGANISM: Homo sapiens

<400> SEQUENCE: 6
gcaatgcggt tctgatactg                                           20
```

PROBIOTICS FOR GUT NEUROMUSCULAR FUNCTIONS

BACKGROUND OF THE INVENTION

The present invention relates to the use of a selected probiotic for the manufacture of a nutritional composition or a medicament to prevent or treat gut pain or gut discomfort related or linked to gut muscular abnormalities. The present invention generally relates the use of a selected probiotic to prevent of treat persistent gut neuromuscular abnormalities, as encountered in many instances.

The present invention further relates to a method of preventing or treating gut pain or gut discomfort and persistent motor dysfunction in the gut.

Probiotics are generally defined as a live microbial food supplement which beneficially affects the host human or animal by improving its intestinal microbial balance. Several different beneficial effects of probiotics have so far been reported or proposed, such as displacement of *Helicobacter* infection (EP 0577 903), enhancement of colonization resistance, especially with regard to *Clostridium* species, reduction of serum cholesterol, influence on the host immune system, for example on the level of the humoral and the cellular immune system.

EP 0768 375 discloses Bifidobacteria that are able to be implanted in the intestinal flora, to adhere to intestinal cells and to competitively exclude pathogenic bacteria on the intestinal cells.

In WO 98/00035 enteral compositions containing several lactic acid bacteria are disclosed, which are shown to stimulate the immune system, as measured by the number of T CD4+ peripheral blood lymphocytes.

When humans and mammalian animals suffer from gut discomfort or gut pain, these often are the symptoms of gut motility disorders, or, in other words, gut neuromuscular abnormalities.

Individuals of any age and in many circumstances are concerned from gut neuromuscular abnormalities. Examples are babies suffering from colic or abdominal recurrent pain, women suffering from gut pain due to hormonal cycle and emotional stress, and many more.

If gut pain and discomfort persists over prolonged time in particularly severe cases and a doctor's advice is sought, it may be that IBS (Irritable Bowel Syndrome) is diagnosed.

In the context of IBS the prior art is not coherent on the effect of probiotics on this particular syndrome. In one recent study (Niedzielin K et al, A controlled, double-blind, randomized study on the efficacy of *Lactobacillus plantarum* 299V in patients with irritable bowel syndrome, European Journal of Gastroenterology & Hepatology 2001, 13:1143-1147) it is found that probiotics may have a role in regulating the motility of the digestive tract.

On the other hand, in the paper of O'Sullivan M A and O'Morain (Bacterial supplementation in the irritable bowel syndrome. A randomized double-blind placebo-controlled crossover study, Dig Liv Dis 2000 May; 32(4):302-4) no significant differences were found between *Lactobacillus casei* strain GG and placebo mean. Other prior art confirms the later finding.

It is an object of the present invention to alleviate any pain, or discomfort related to persistent altered neuromuscular control and motor function in the guts (gut-neuromuscular abnormalities).

The present invention has the general objective to reduce and/or alleviate gut-neuromuscular abnormalities associated with any possible circumstance in an individual's life.

SUMMARY OF THE INVENTION

Remarkably, probiotic micro-organisms, their metabolites and/or their growth substrate affect neuromuscular control in the intestines. In particular, it was shown that specific probiotics are useful to reduce persistent neuromuscular abnormalities in the gastrointestinal tract. This effect is strain-dependent.

Consequently, in a first aspect the present invention provides the use of a selected probiotic or a mixture of selected probiotics in the manufacture of a nutritional composition or a medicament to prevent or treat gut pain or gut discomfort related or linked to gut muscular abnormalities.

In a second aspect the invention provides the use of a selected probiotic or a mixture of selected probiotics in the manufacture of a nutritional composition or a medicament to prevent or treat persistent motor dysfunction in the gut.

In a third aspect the invention provides the use of a selected probiotic or a mixture of selected probiotics in the manufacture of a nutritional composition or a medicament to prevent of treat persistent gut neuromuscular abnormalities.

In a fourth aspect, the present invention provides the use of a selected probiotic or a mixture of selected probiotics in the manufacture of a nutritional composition or a medicament to treat or prevent Irritable Bowel Syndrome (IBS).

In a fifth aspect, the present invention provides the use of a selected probiotic or a mixture of selected probiotics in the manufacture of a nutritional composition or a medicament to treat or decrease sequellae after infection of the gut.

In a sixth aspect, the present invention provides a method of preventing or treating gut pain or gut discomfort related or linked to gut muscular abnormalities comprising the step of enterally administering to a human or an animal an effective amount of a selected probiotic or a mixture of selected probiotics.

In a seventh aspect, the present invention provides a method of preventing or treating persistent motor dysfunction in the gut comprising the step of enterally administering to a human or an animal an effective amount of a probiotic or a mixture of selected probiotics.

An advantage of the present invention is that it provides a possibility to treat or prevent gut-neuromuscular abnormalities and the associated symptoms, gut problems or disease states.

Another advantage of the present invention is that it provides a possibility to treat or prevent gut-neuromuscular abnormalities without administration of pharmaceutical drugs, but on the base of food grade probiotic micro-organisms or their derivatives.

It is an advantage that gut pain or discomfort occurring in many different instances of an individual's life may be treated or prevented. Gut pain or discomfort associated with gut muscular abnormalities occurs, for example, with sportspeople or athletes during intense exercise, including exercise induced cramping. Other examples when gut discomfort is caused by gut-neuromuscular abnormalities are indicated below.

Additional features and advantages of the present invention are described in, and will be apparent from, the following Detailed Description of the Invention and the figures.

DETAILED DESCRIPTION OF THE INVENTION

Figure 1:
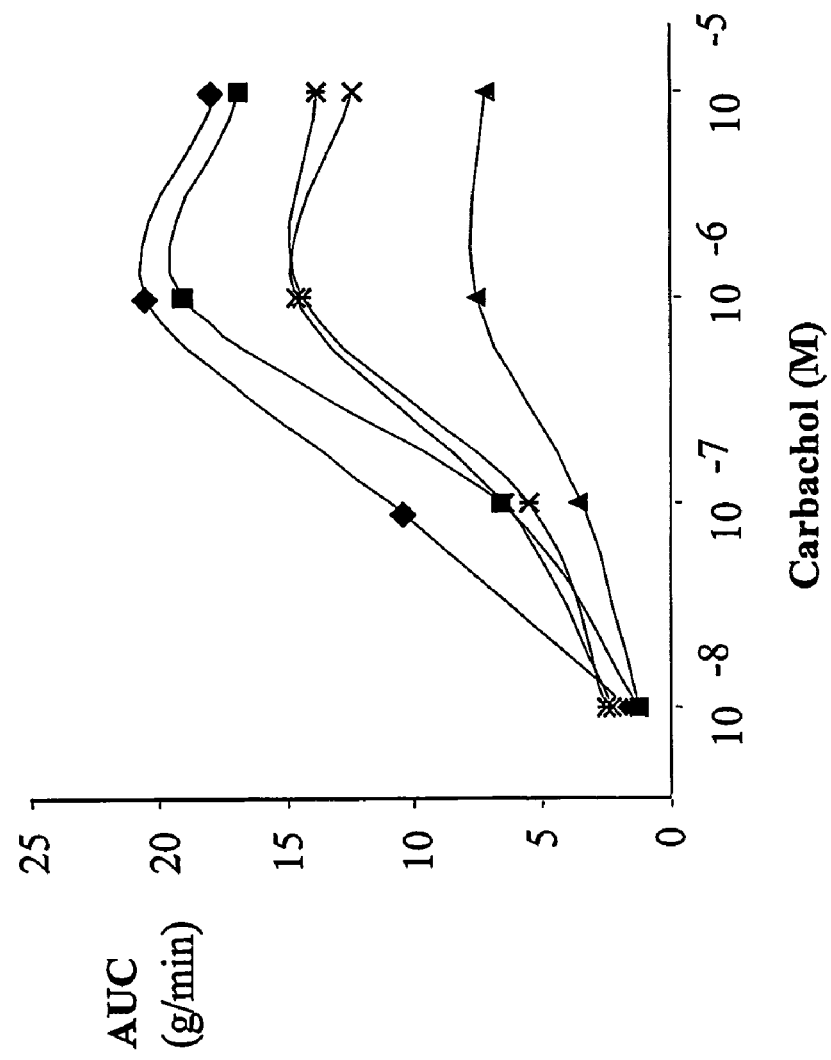
FIG. 1 shows the area under curve (AUC) of contraction intensity of gut muscle tissue taken from a host organism, which was infected by a nematode parasite and, 10 days after infection, fed with different probiotics and a control. The stimulation occurred with carbachol at different concentrations (details are given in Example 2). The AUC is a measure for the intensity and pertinacity of the contraction of the gut muscle and a measure for the degree of neuromuscular abnormality developed during infection. The symbols have the following meaning: ♦ control, ■ *Lactobacillus acidophilus* (*johnsonii*), ×*Bifidobacterium longum*, * *Bifidobacterium lactis*, ▲ *Lactobacillus paracasei*. It can be seen that probiotics generally decrease the AUC, whereby different strains have more and less pronounced effect.

Within the context of this specification the word "comprises" is taken to mean "includes, among other things". It is not intended to be construed as "consists of only".

For the purpose of the present invention, the term "selected probiotic micro-organisms", or simply "selected probiotic" refers to any micro-organism that is able to exert the beneficial effects reported herein, or to a combination or mixture of such probiotics. A probiotic may thus be selected from known probiotic strains. However, a micro-organism so far not known to have probiotic properties may prove to have the beneficial effect according to the present invention and is therefore included within the term probiotic.

Within the context of the present invention, the term "nutritional composition" is intended to encompass any consumable matter. Hence, it may be a product intended for the consumption by humans, but the term also encompasses products to be consumed by animals, for example pets, such as dogs, cats, rabbits, guinea pigs, mice, rats, birds (for example parrots), reptiles and fish. However, the term also includes food to be consumed by other domesticated animals, for example feed products for livestock, for example, cattle, horses, pigs, sheep, goats, buffaloes, camels, and the like.

A nutritional composition may be a food product intended for human consumption, for example, a beverage, a drink, a bar, a snack, an ice cream, a dairy product, for example a chilled or a shelf-stable dairy product, a confectionery product, a cereal product such as a breakfast cereal, a frozen product intended for consumption after heating in a microwave or an oven, a ready-to-eat product, a fast food or a nutritional formula.

A nutritional formula encompasses any nutritionally complete or supplementary formulation. It may be a generally applicable nutritional formula, an infant or baby formula, a formula for elderly patients, for extensive care patients, or a specially adapted formula for patients suffering from a specific disease, for example. For example the nutritional formula may be adapted to patients suffering from nutrition-linked problems, such as Crohn's disease, hyperglycemia, obesity, weight loss, diarrhea, constipation, phenylketonuria, hepatitis, acute or chronic renal failure, just to mention a few. Such formulas may be reconstitutable, that is, present in a dried form, or ready to drink, in the form of liquid formulas, for example.

In the context of the present invention, the term "gut-neuromuscular abnormalities" encompasses all pain or discomfort related symptoms that are linked to abnormal or disturbed gut-muscle contractions, contractility or motility. For example, these abnormalities are associated with disturbed distension or defecation, with colic in babies and/or infants, with gut invaginations in humans or pets, with disturbed transit time throughout the intestine, after infection of the gut with parasites, such as nematodes and pathogenic bacteria, for example.

Further gut-neuromuscular abnormalities in the context of the present invention include those associated with infancy as for example part of the problems of infant colic, those associated with exercise including exercise induced cramping and neuromuscular problems associated with intensive exercise and athletics, those associated with pregnancy and disturbances associated with childbirth, those associated with clinical patients possessing unrelated injuries, trauma and infections but whose clinical treatment or situation cause a loss of intestinal neuromuscular function including antibiotics, immobilization and parenteral or enteral feeding, those associated with aging and the loss of neuromuscular control associated with reduced activity, low fiber diets and changing microflora, those associated with unusual dietary or lifestyle habits including ethanol consumption, drugs exhibiting neuromuscular side effects, altered gravity of astronauts, intense heat or cold and problems of rehydration.

"Persistent motor dysfunction" is equivalent to gut-neuromuscular abnormalities that typically follow infection of human or animal gastro-intestinal tract by pathogenic organisms, such as nematodes, cestodes and certain bacteria, for example, *Helicobacter pylori* or *Salmonella*. Persistent motor dysfunction may also occur during or after inflammation due to other causes.

"Sequellae" are abnormalities or deviations from a healthy state that persist after infection, even if parasites or infective agents have been eliminated from the host. They are thought to be in general irreversible damages that were caused to the host.

"Probiotic-derived material", in the context of the present invention, includes living or dead probiotics, the medium obtained by fermentation with a probiotic, the metabolites found in the medium after fermentation and its derivatives, such as concentrates, for example, the fermentation substrate, supernatant and/or retentate of the medium after elimination of probiotic bacteria by filtration or centrifugation, for example.

In an embodiment of the present invention, the selected probiotics are selected from the group consisting of *Lactobacillus johnsonii* (CNCM I-1225), *Bifidobacterium longum* (CNCM I-2170), *Bifidobacterium lactis* (German Culture Collection: DSM20215), *Lactobacillus paracasei* (CNCM I-2116, CNCM I-1292), and mixtures thereof.

In a further embodiment of the present invention the probiotics include dead probiotic bacteria, fermentation substrate and/or probiotic-derived material.

In another embodiment of the present invention the probiotics also include their fermentation substrate, such as prebiotics. The skilled person is usually aware of the fermentation substrates of probiotics. Bifidobacteria, for example, can utilise inulin and/or oligofructose as a fermentation substrate.

Selection of the Probiotic

As a probiotic, any suitable micro-organism may be selected. Preferably, the probiotic according to the present inventions are selected from micro-organisms exerting beneficial effects on health and welfare on humans or animals.

The literature mentions some of the micro-organisms from which the probiotics according to the present invention may be selected. For example, EP 0 862 863A2, in particular on page 3, lines 25-37, comprises a list from which the probiotic according to the present invention may be selected.

Examples of suitable probiotic micro-organisms include yeasts such as *Saccharomyces, Debaromyces, Candida, Pichia* and *Torulopsis*, moulds such as *Aspergillus, Rhizopus, Mucor*, and *Penicillium* and *Torulopsis* and bacteria such as the genera *Bifidobacterium, Bacteroides, Clostridium, Fusobacterium, Melissococcus, Propionibacterium, Streptococcus, Enterococcus, Lactococcus, Kocuria, Staphylococcus, Peptostrepococcus, Bacillus, Pediococcus, Micrococcus, Leuconostoc, Weissella, Aerococcus, Oenococcus* and *Lactobacillus*.

Specific examples of suitable probiotic micro-organisms are: *Aspergillus niger, A. oryzae, Bacillus coagulans, B. lentus, B. licheniformis, B. mesentericus, B. pumilus, B. subtilis, B. natto, Bacteroides amylophilus, Bac. capillosus, Bac. ruminocola, Bac. suis, Bifidobacterium adolescentis, B. animalis, B. breve, B. bifidum, B. infantis, B. lactis, B. longum, B. pseudolongum, B. thermophilum, Candida pintolepesii, Clostridium butyricum, Enterococcus cremoris, E. diacetylactis, E. faecium, E. intermedius, E. lactis, E. muntdi, E. thermophilus, Escherichia coli, Kluyveromyces fragilis, Lactobacillus acidophilus, L. alimentarius, L. amylovorus, L. crispatus, L. brevis, L. casei, L. curvatus, L. cellobiosus, L. delbrueckii* ss. *bulgaricus, L. farciminis, L. fermentum, L. gasseri, L. helveticus, L. lactis, L. plantarum, L. johnsonii, L. reuteri, L. rhamnosus, L. sakei, L. salivarius, Leuconostoc mesenteroides, P. cereviseae (damnosus), Pediococcus acidilactici, P. pentosaceus, Propionibacterium freudenreichii, Prop. shermanii, Saccharomyces cereviseae, Staphylococcus carnosus, Staph. xylosus, Streptococcus infantarius, Strep. salivarius* ss. *thermophilus, Strep. thermophilus, Strep. lactis.*

For example, a probiotic strain or strains may be selected from the group comprising *Bacillus licheniformis* (DSM 5749), *B. subtilis* (DSM 5750), *Bifidobacterium lactis* (DSM20215), strains of *Enterococcus faecium* (e.g. NCIMB 10415; NCIMB 11181; NCIMB 30098; DSM 3520; DSM 4788; DSM 4789; DSM 5464; DSM 7134; CECT 4515), *E. mundtii* (CNCM MA 27/4E), strains of *Saccharomyces cereviseae* (e.g. BCCM/MUCL 39885; CBS 493 94; CNCM I-1077; CNCM I-1079; NCYC Sc47), *Lactobacillus casei* (NCIMB 30096), *L. farciminis* (CNCM MA 67/4 R), *L. johnsonii* (1-1225 CNCM), *Lactobacillus paracasei* (I-2116 CNCM), *L. plantarum* (CNCM I-840), *L. rhamnosus* (DSM 7133), *P. acidilactici* (CNCM MA 18/5 M), *Streptococcus infantarius* (CNCM I-841), *Streptococcus thermophilus* (Chr. Hansen, see examples), and mixtures thereof, for example.

Further examples of probiotic species with exemplary, deposited strains of the species according to the present invention may be selected from the group comprising *Lactobacillus reuteri* (CNCM I-2452, CNCM I-2448, CNCM I-2450, CNCM I-2451), *Lactobacillus rhamnosus* (CNCM 1-2449), *Lactobacillus acidophilus* (CNCM 1-2453), and mixtures thereof. The strains mentioned in this paragraph may be particularly suitable for pets.

An effective probiotic according to the present invention may be selected by a screening method from the above list. While any suitable screening method can potentially be exploited, the method developed in Barbara G, Valiance B A, Collins S M Persistent intestinal neuromuscular dysfunction after acute nematode infection in mice, Gastroenterology 1997; 113: 1224-1232 proves to be relatively quick. The reference discloses a model for measuring intensity of gut neuromuscular abnormalities.

Consequently, a suitable probiotic may be selected by the steps of selecting at least one organism of a single animal species or humans that suffers from gut-neuromuscular abnormalities, administrating enterally to the organism probiotic-derived material, measuring a first contractility from gut muscle tissue of the organism, comparing the first contractility to a second contractility of a negative control, and, selecting a probiotic strain that caused muscle-tissue of the organism that consumed the probiotic to have reduced first contractility if compared to the negative control.

The term "negative control" in the context of the screening for selecting specific probiotic strains, is intended to mean gut-muscle tissue from a an organism suffering from gut-neuromuscular abnormalities, whereby the organism was not enterally administered probiotic-derived material.

The screening comprises a step of measuring a first contractility from gut muscle tissue of the organism and, furthermore, a step of comparing the first contractility to a second contractility of the negative control.

The contractility may be measured by any suitable method. For example, the method of Barbara G, Vallance B A, Collins S M (see above) is used. See especially the chapters "Tissue Preparation for Contractility Studies", "Measurement of Contraction" "Parameters of Electrical Field stimulation", Drugs and Solutions" and "Data Expression and Statistical Analysis", pages 1225-1226, which are incorporated herein by reference.

Accordingly, contractility is measured in vitro, that is by dissecting gut segments, for example of the proximal jejunum, fixing the segments in a suitable way in a tissue bath, inducing a muscle contraction, for example by a chemical or electric stimulant, and recording the contraction with a suitable data processing unit.

Figure 3:
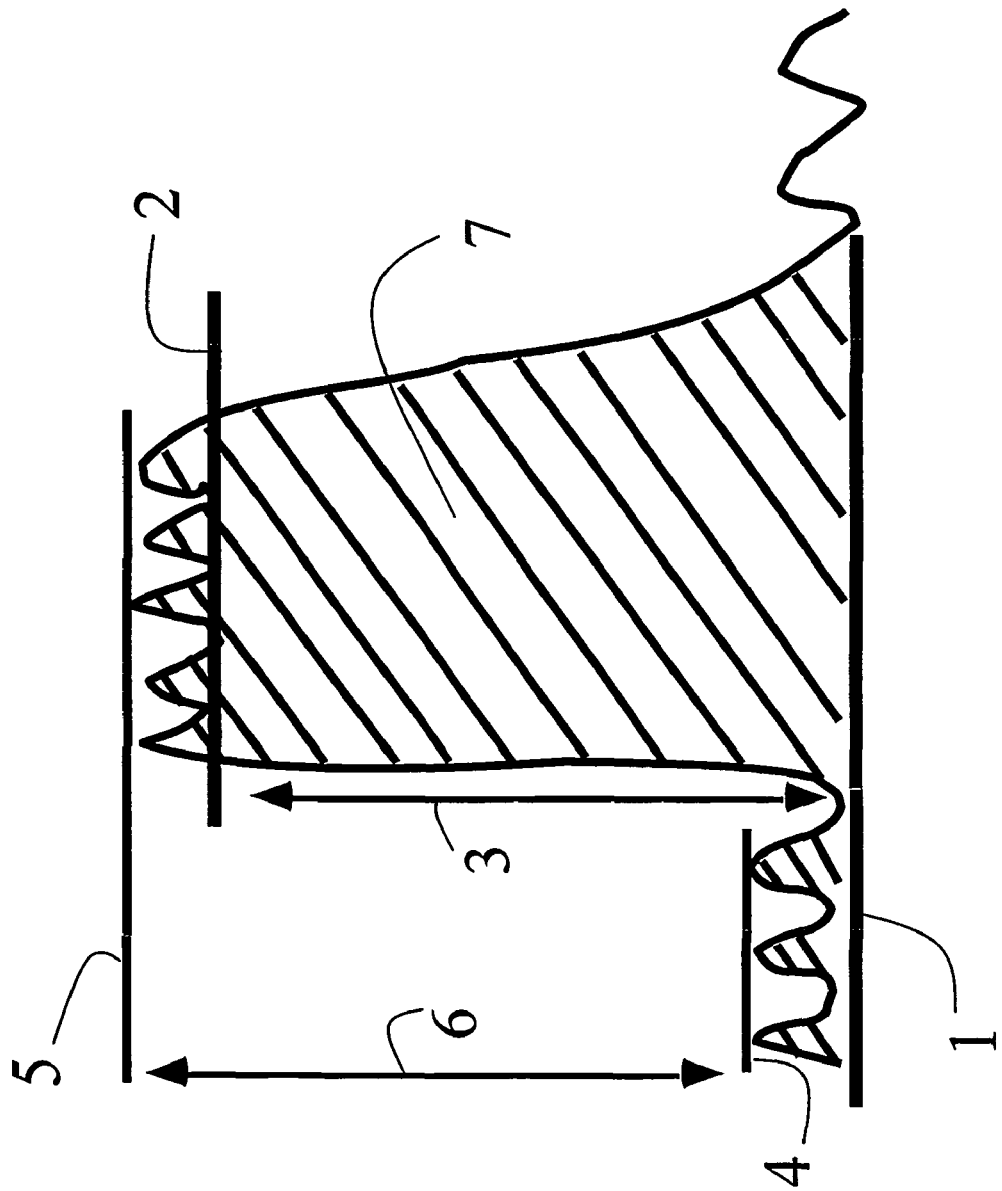
FIG. 3 visualises the concepts of the method used to determine neuromuscular abnormalities after infection. The curve shows the record of a stimulation of a muscle in vitro. Before stimulation, a basal tone (1) and a basal phasic (4) are recorded. After stimulation, a contraction of the muscle occurs, which is recorded as a stimulated tone (2) and a stimulated phasic contraction (5). Also an area under the curve (AUC) can be calculated (7). For statistics, the tonic contraction (3), phasic contraction (6) and the AUC (7) of control versus treated were compared.

The measurements of the basal tone (1), stimulated tone (2) and tonic contraction (3), as well as basal phasic (4), stimulated phasic contraction (5), phasic contraction (6) and area under the curve (7), as illustrated in FIG. 3 may serve as parameters for contractility.

The selected probiotic according to the invention is a probiotic, which, following the above screening method, reduces gut-muscle contractility in an organism suffering from gut-neuromuscular abnormalities if compared to the negative control, for example.

In an embodiment of the present invention, the selected probiotic is a probiotic, which is capable, in a mouse model, to affect a pathogen-induced immune response in that it significantly reduces Th2-released cytokines. Preferably, Th2 released cytokines are IL-4 and/or IL-13.

"Significant", in the context of the present invention, refers to a statistically significant difference for $P<0.1$, preferably $p<0.05$, which is obtained when comparing infected mice fed with probiotics (treatment) against a negative control.

In general, cytokines may be measured in a longitudinal myenteric muscle preparation (LMMP) at a determined period after infection. Preferably, cytokines are measured in LMMP 14 days after infection. Cytokine concentration may be measured using commercially obtainable kits and following manufacturers directions.

A preferred method of assessing whether or not a probiotic is capable of significantly reducing Th2-released cytokines includes a mice model and is given below.

Female NIH swiss mice (6-8 weeks of age) are each gavaged with 375 larvae of *Trichinella spiralis* (see method of Barbara G. et al, above).

To determine influence of probiotics, infected mice were gavaged daily from day 10 to 21 post-infection with 100 µl of $10^{10}$ probiotic micro-organisms (bacteria, yeast, etc), with 100 µl MRS as a negative control.

An LMMP may be prepared by dissecting the entire jejunum, rinsing in cold sterile PBS, and cutting into 4 sections. The mesentery is removed and pieces of intestine are mounted onto a glass rod. The muscle layer is scraped off using a clean cotton swab, snap frozen and stored at $-70°$ C. until analysis. Successful isolation of muscle may be confirmed by histologic evaluation. Muscle tissue is placed in 1 ml. of lysis buffer containing 10% NP-40, 10 mg/ml PMSF in isopropanol, 1 mg/ml aprotinin and 1 mg/ml leupeptin. After the tissue is homogenized, total protein concentration is measured (Bio-RAD protein assay, Hercules, Calif., USA) and samples are aliquotaed and stored at $-70°$ C. for further analysis.

Concentration of IL-4 and IL-13 (Th2-cytokines) and other inflammatory mediators TGF-b1 and PGE2 may be measured in LMMP using commercial kits (Quantikine M Murine, Minneapolis, Minn., USA) following manufacturer's directions.

In another embodiment of the present invention, the probiotic is a probiotic, which is capable, in a mouse model, to affect a pathogen-induced inflammation in that it significantly reduces COX-2, TGF-β1 or PGE2 expression or concentration in LMMP.

TGF-β1 or PGE2 concentration may be measured by analyzing LMMP using commercially obtainable kits as indicated above for IL-4 and IL-13.

A preferred method for assessing significant differences, in particular of TGF-β1 and COX-2 expression in LMMP of infected mice is given below:

Messenger RNA expression of TGF-β and COX-2 is measured in LMMP 14 days post infection. Total RNA is isolated from LMMP using the single-step method (Chonczynski P, Sacci N "Single step method of RNA isolation by acid guanidium thiocyanate-phenol-chloroform extraction," Ann Biochem 162: 156-159; 1987).

Reverse transcription and PCR reactions is performed as described by Verdu E F et al. (Modulatory effect of estrogen in two murine models of experimental colitis. Am J Physiol gastrointest Liver Physiol 2000; 283: G27-36).

The following primers are used. HPRT (Hypoxanthine guanine phosphoribosyl atransferase, used as control for standardization): sense 5'-GTT GGA TAC AGG CCA GAC TTT GTT G-3' (SEQ ID No. 1), antisense 5'-GAT TCA ACT TGC GCT CAT CTT AGG C-3' (SEQ ID No. 2) (Svetic A, "Cytokine expression after immunization", J Immun 147: 2391-7). TGF-β: sense 5'-TCA CCC GCG TGC CTA ATG GT-3' (SEQ ID No. 3) and antisense 5'-GGA GCT GAA GCA ATA GTT GG-3' (SEQ ID No. 4) (Derynck R, Rhee L, Nucleic Acid Res 1987; 15: 3187-97); COX-2: sense 5'-TGG TGC CGG GTC TGA TGA TG-3' (SEQ ID No. 5) antisense 5'-GCA ATG CGG TTC TGA TAC TG-3' (SEQ ID No. 6) (Gustafson-Svard et al, Cyclooxygenase-1 and cyclooxygenase-2 gene expression in human colorectal adenocarcinomas and azomethane induced colonic tumours in rats. Gut 1996; 38: 79-84);

To exclude the amplification of genomic DNA contaminating the samples, experiments were also performed using RNA as substrate for PCR. After amplification, 15 µl of PCR products were separated electrophoretically in 2% agarose gel, visualized by ethidium bromide staining and photographed using a Polaroid land film type 55 (Kodak, Rochester, N.Y.). The negatives were used for densitometrical quantification of band intensity using the Kodak Digital Science 1D 2.0 Image Analysis Software. The results were normalized to the housekeeping HPRT gene and expressed as ratio of cytokines to HPRT mRNA expression.

In an embodiment of the present invention, the selected probiotic is a *Bifidobacterium*. Preferably, it is a *Bifidobacterium lactis* or a *Bifidobacterium longum*.

In a further embodiment of the present invention, the selected probiotic is a *Lactobacillus paracasei*.

In still a further embodiment of the present invention, the selected probiotic is selected from the group consisting of *Bifidobacterium longum* (CNCM 1-2170), *Bifidobacterium lactis* (German Culture Collection: DSM20215), *Lactobacillus paracasei* (CNCM I-2116, CNCM I-1292), and mixtures thereof.

CNCM I-1292 was deposited on Mar. 29, 1993 under the Budapest Treaty at the Pasteur Institute, Collection Nationale de Culture de Microorganismes ("CNCM"), 28 rue du Docteur Roux, F-75724 Paris, Cedex 15, France.

In yet another embodiment of the present invention, the probiotic includes dead probiotic bacteria, fermentation substrate and/or probiotic-derived material.

Optionally, the probiotics also include their fermentation substrate, such as prebiotics. The skilled person is usually aware of the fermentation substrates of probiotics. Bifidobacteria, for example, can utilize inulin and/or oligofructose as a fermentation substrate.

Probiotic Preparation

The skilled person is aware of how to produce the selected probiotic micro-organism. They may be either obtained commercially or they may be produced generally by a fermentation process and, optional, drying. Specific strains often have particular media or substrate preferences, which the skilled person knows about.

The micro-organisms may be in a dried form, or for example in a spore form for micro-organisms which form spores. The drying of micro-organisms after production by fermentation is known to the skilled person. See for example, EP 0 818 529 (SOCIETE DES PRODUITS NESTLE), where a drying process of pulverisation is described, or WO 0144440 (INRA). Usually, bacterial micro-organisms are concentrated from a medium and dried by spray drying, fluidised bed drying, lyophilisation (freeze drying) or another adequate drying process. For example, micro-organisms are mixed with a carrier material such as a carbohydrate, for example sucrose, lactose or maltodextrin, a lipid or a protein, for example milk powder during or before the drying.

However, the micro-organisms need not necessarily be present in a dried form. It may also be suitable to mix them directly after fermentation with a food product to optionally perform a drying process thereafter. Such an approach is disclosed in WO (Filing Nr: PCT/EP02/01504) (SOCIETE DES PRODUITS NESTLE). Likewise, probiotics may, theoretically, also be consumed directly after fermentation. Further processing, for example for the sake of the manufacture of convenient food products, is not a precondition for the beneficial properties of probiotics.

Many probiotics suitable to carry out the present invention are commercially available and may be obtained in a powdered form various suppliers, for example, *Bifidobacterium lactis* (DSM 20215) may be obtained from Ch. Hansen.

The skilled person is aware of various different suppliers of probiotics. Some suppliers furnish the probiotics in a specific encapsulated form in order to ensure a high survival rate of the micro-organisms during passage through the gastrointestinal tract or during storage or shelf life of the product.

An example of a product comprising micro-organisms having an increased storage stability without undue loss is described in EP 0 180 743 and also in WO (Filing Nr: PCT/EP02/01504) (SOCIETE DES PRODUITS NESTLE).

The probiotics according to the present invention may be enterally consumed in any form. They may be added to a nutritional composition, such as a food product. On the other hand, they may also be consumed directly, for example in a dried form or directly after production of the biomass by fermentation.

Probiotics may, for example, be consumed in the form of a fermented, dairy product, such as a chilled dairy product, a yoghurt, or a fresh cheese. In these later cases, the probiotic may be used directly also to produce the fermented product itself and has therefore at least a double function: the probiotic functions within the context of the present invention and the function of fermenting a substrate such as milk to produce a yoghurt.

If the probiotic is added to a nutritional formula, the skilled person is aware of the possibilities to achieve this. Dried, for example spray dried bacteria, such as obtainable by the process disclosed in EP 0 818 529 may be added directly to a nutritional formula in powdered form or to any other, optionally dried, food product. For example, a powdered probiotic preparation may be added to a nutritional formula, breakfast cereals, salads, a slice of bred prior to consumption.

Nutritional formulas comprising specific probiotics are currently commercially available. For example, follow-up formulas comprising probiotics are commercialized by Nestlé, such as the "NAN2 or the NIDINA2—with Bifidus" product, is especially adapted to infants, may be used for the purpose of the present invention, as long as effective amounts are provided.

Alternatively, dried probiotics may be added to a liquid product, for example a beverage or a drink. If it is intended to consume the bacteria in a living state, the liquid product comprising the probiotics should be consumed relatively quickly upon addition of the probiotics. However, if the bacteria are added to a shelf-stable product, quick consumption may not be necessary, so long as the probiotics are stable in the beverage or the drink.

WO 98 10666 discloses a process of drying a food composition and a culture off probiotic bacteria conjointly. Accordingly, probiotics may be dried at the same time with juices, milk-based products or vegetable milks, for example, yielding a dried product already comprising probiotics. This product may later be reconstituted with an aqueous liquid.

Quantity of Probiotics

Although it is not mandatory, probiotic bacteria may be consumed in the living state with the intention that the probiotic micro-organisms arrive intactly in the small and large intestines the latter of which may be colonized. If this is the case, a sufficient dose of living bacteria is usually consumed per day in order to achieve successful colonization. The skilled person is aware of these daily doses, which depend on the micro-organisms but generally lie in the range of $10^6$ to $10^{14}$, preferably $10^7$ to $10^{13}$ cfu per day.

In the context of the present invention, the effective amount of living probiotic to be administered to a human having a body weight of about 65 kg will preferably be in the range of $10^{10}$ to $10^{14}$, more preferably, $10^{11}$ to $10^{13}$, most preferably $1-4\times10^{12}$ cfu per day.

The preferred amount of living probiotic corresponds to approximately one 2 dl-yoghurt pot per day, prepared with a probiotic strain, as commercially available. One daily serving of a food product, or, if several daily servings are preferred, all the servings together will usually be enriched with an effective amount of probiotics as indicated above.

However, the teaching of the present invention may also be achieved with dead probiotics, with the fermented media or simply with the substrate for the probiotics, which usually is prebiotic fibre.

Hence, the fermented media, even if essentially free of probiotics but comprising metabolites of probiotics may be used to work the present invention.

In other words, dead or living probiotics, their medium, substrate or metabolites may be directly added to food products in the same or a similar way as set forth above for living probiotics more specifically. The fermented medium, substrate or metabolites may separated from the bacteria after fermentation by centrifugation or filtration, for example. The supernatant or the filtrate may then be concentrated, chilled, frozen, dried, for example spray dried or directly used for enteral administration to an individual. If fermented medium is dried, it may be powdered and, as described above for the living probiotics, added to any food product.

If supernatant or fermentation medium is to be administered to a human, the effective amount is in the range of 0.5 to 3 dl, preferably 1 to 2 dl of growth medium, harvested after 30 to 50 hrs, preferably 45 to 50 hrs of bacterial growth. When density of bacteria is estimated at an OD600 nm, an OD of 2 to 7 is routinely obtained, which represents the respective growth of 2 to $7\times10^8$ bacteria per ml. The supernatant may be administered after removal of the bacteria by filtration, for example.

The effective amount of supernatant corresponds to a pot of 1 to 2 dl yoghurt a day, prepared with a selected probiotic, as commercially available.

With animals, such as pets, the corresponding effective amount of living bacteria or supernatant is calculated as a function of body weight.

It is also possible to homogenize the fermented medium including probiotics and to further process the normally destroyed probiotics together with the medium.

As already indicated, substrate of probiotics, such as dietary fibre that promotes specific probiotics may be used to work the present invention. This is a way of achieving the effects according to the present invention indirectly. By promoting growth of specific probiotic strains in the intestinal tract, the same effects as reported herein may be achieved.

The following examples are given by way of illustration only and in no way should be construed as limiting the subject matter of the present application.

Examples 1 and 2 below have the goal to examine whether gut abnormalities, which develops after a transient intestinal mucosal infection and gut-neuromuscular abnormalities in general can be prevented or treated by probiotic supplementation.

To examine these questions a mouse model was used that is characterized by persistent neuromuscular abnormalities after an acute episode of *Trichinella spiralis* infection It was thus found that probiotic bacteria may reverse persistent gut-neuromuscular abnormalities after intestinal infection.

The results suggest for the first time that probiotic bacteria can interfere with parasite load during intestinal infections. Also, that some of the long-term gastrointestinal complications arising from these infections can be reversed by probiotics even when administration starts after the establishment of parasite infection. These effects are, as was shown for the first time, highly dependent on the probiotic strain.

Example 1

Probiotics for the Prevention of *T. spiralis* Infection in Mice

Materials and Methods

The following, at the "Collection Nationale de Cultures de Microorganismes" (CNCM) deposited strains, as well as a commercially available probiotic strain were taken for the experiment.

Lactobacillus acidophilus (johnsonii) (CNCM I-1225)
Lactobacillus paracasei CNCM I-2116)
Bifidobacterium longum (CNCM I-2170)
Bifidobacterium lactis (German Culture Collection: DSM20215) purchased from Christian Hansen BioSystems A/S(CHL), 10-12 Boge Alle, P.O Box 407, DK-2970 Horsholm, Denmark.

The probiotic preparations and two controls, medium (MRS) or phosphate buffer saline (PBS), were gavaged to female NIH swiss mice (n=5 per group) daily for 10 days prior to *T. spiralis* infection (375 larvae). Probiotic administration continued throughout the experiment. Nine days after *T. spiralis* infection, mice were euthanised for worm counts and myeloperoxidase activity (MPO).

The daily gavaged amounts were $1 \times 10^9$ bacteria/100 W growth medium/mouse/day of each bacteria and 100 µl filtered growth medium/mouse/day in experiments with supernatant only.

Results

There were no differences in worm counts between mice preventively treated with MRS or PBS, therefore all further experiments have used MRS as a single control group.

It was found that mice pretreated with the *Bifidobacterium lactis* strain tended to have lower worm counts than mice pretreated with MRS and PBS. The *Lactobacillus acidophilus*-strain, on the other hand, appears to increase worm load. The rest of the strains—for the time period and doses tested—do not appear to affect significantly worm load.

In conclusion, it was found that different probiotic strains have differential effects on worm load when administered preventially. Specific probiotic strains, for example the *Bifidobacterium lactis* strain, are capable of reducing infection-load by intestinal parasites, such as nematodes.

Example 2

Probiotics for the Treatment of the Sequellae of *T. spiralis* Infections in Mice Material and Methods In the second experiment, mice were first infected with *Trichinella spiralis* (375 larvae), and gavaged daily with the five probiotic above or MRS from day 10 to day 21 post infection, then mice were euthanised and tissue was taken for in vitro contractility experiments. In the *T. spiralis* model, despite parasite eviction and mucosal intestinal inflammation resolution 21 days post infection, neuromuscular abnormalities (hypercontractility) persist.

Neuromuscular function was assessed by contractility measurements in vitro after pharmalogical (carbachol) or electrical stimulation (EFS) of intestinal tissue placed in muscle baths. The method used is that according to Barbara G, Vallance B A, Collins S M Persistent intestinal neuromuscular dysfunction after acute nematode infection in mice. Gastroenterology 1997; 113: 1224-1232. See especially the chapters "Tissue Preparation for Contractility Studies" and "Measurement of Contraction".

Accordingly, a small bowel section is taken from the mice and arranged in a oxygenated (95% $O_2$/5% $CO_2$) Krebs' solution at 37° C. The opposite ends of the bowel section are fastened. One end of the tissue was connected to an isometric force transducer (model FT03C; Grass, Quincy, MA), and the other to the armature of the bath. Responses were recorded on a Grass 7E polygraph. Stimulation occurred with EFS and carbachol (for details see reference above). The stimulated contractions are analysed by computer, whereby a basal tone, a phasic contraction, a tonic contraction and a maximum tension directly after contraction was measurered and an aera under curve was calculated.

FIG. 3 visualises the concepts of basal tone (1), stimulated tone (2) and tonic contraction (3), as well as basal phasic (4), stimulated phasic contraction (5), phasic contraction (6) and area under the curve (7).

Results

FIG. 1 shows the area under curve, which takes into account the period of contraction after stimulation and the tension of contraction within this period. A clear difference (lower area under curve) between mice fed with the probiotic strains mentioned above and the control is found, showing that in the first case the contractions after stimulation are shorter and/or less tense. The symbols in FIG. 1 have the following meaning: ♦ control, ■ *Lactobacillus acidophilus* (*johnsonii*), ×*Bifidobacterium longum*, * *Bifidobacterium lactis*, ▲ *Lactobacillus paracasei*.

Figure 2:
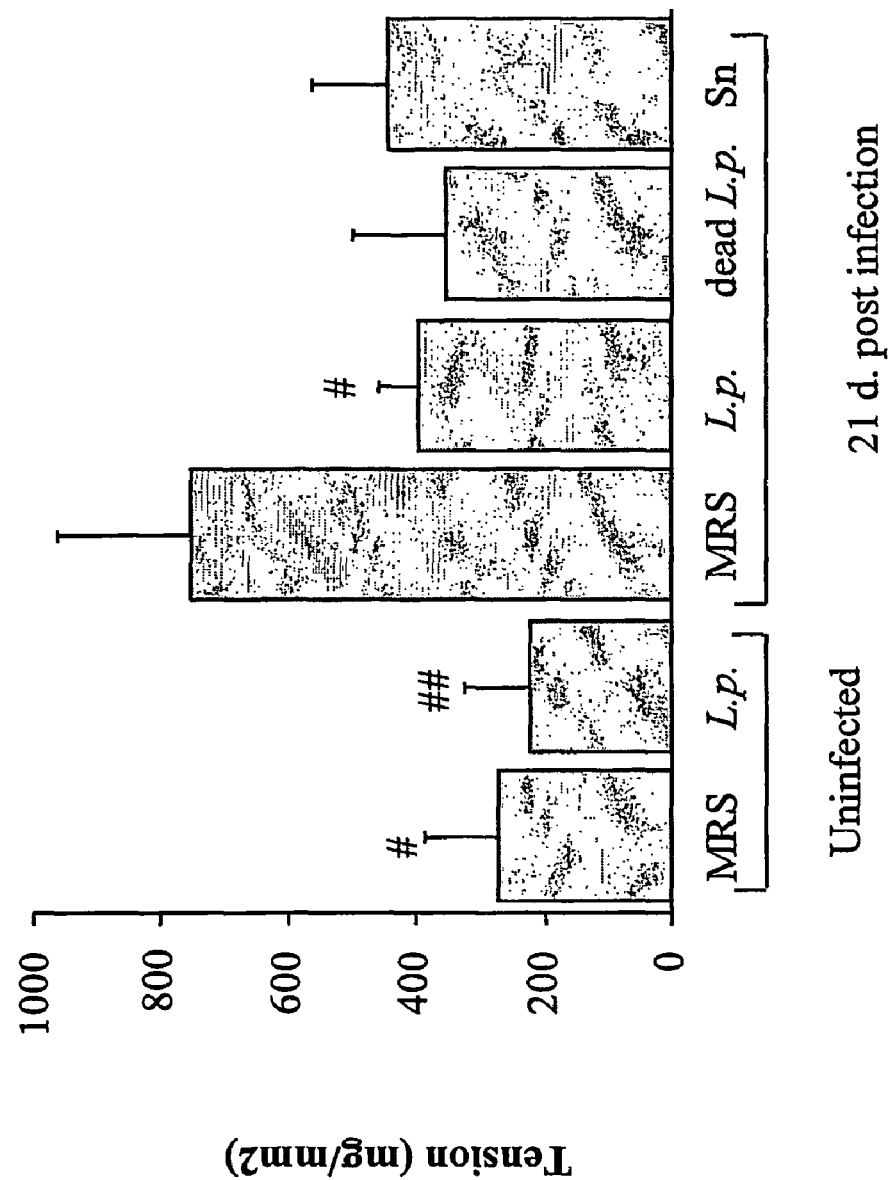
FIG. 2 shows tonic contraction (A) and phasic contraction (B) of muscle tissue as described for FIG. 1, but stimulated by an electric field and compares host organisms fed with the probiotic strain *Lactobacillus paracasei* (CNCM I-2116) in a living state (L.p.), dead state (dead L.p.), and only the supernatant of the medium (Sn). The terms tonic increase and phasic contraction are explained in Example 2 and FIG. 3. As can be seen, all probiotic-derived feeds (living or dead bacteria, supernatant) have clearly lower tonic increase and phasic contraction than the control (MRS).
Figure 2:
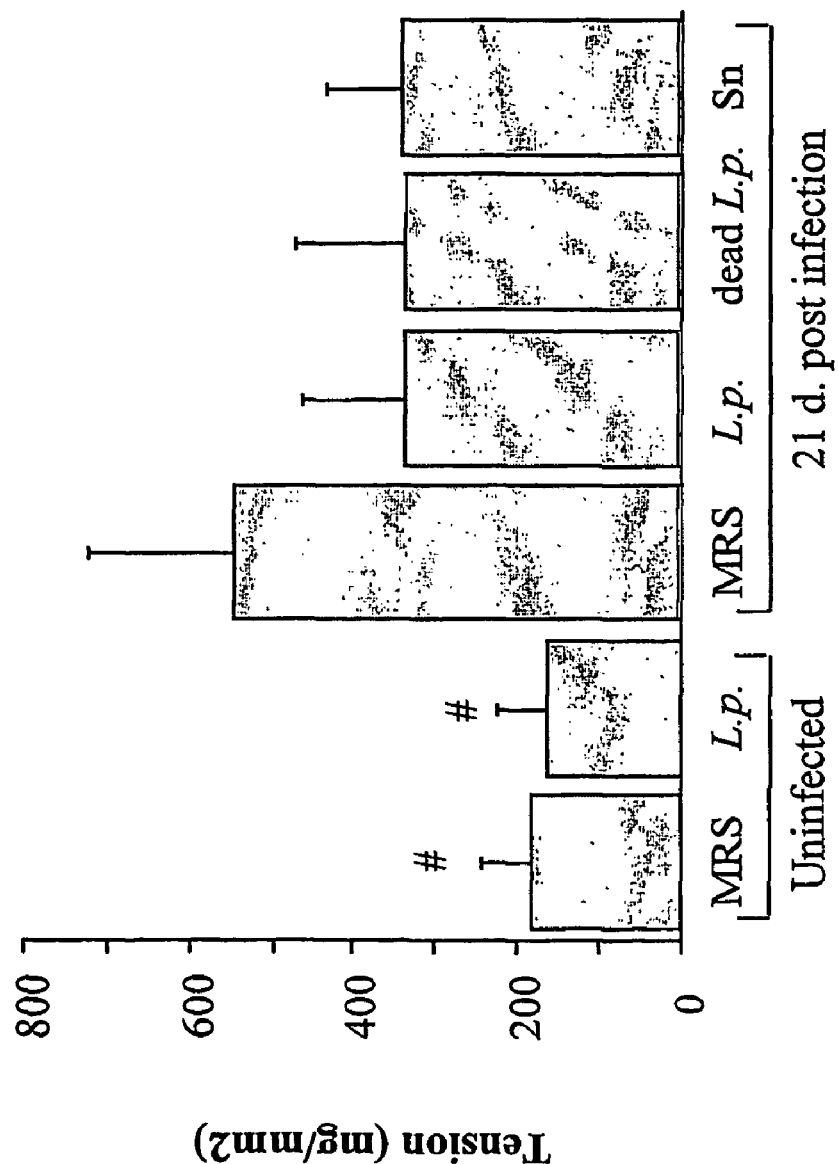

FIG. 2 shows tonic contraction (A) and phasic contraction (B) of muscle tissue as described for FIG. 1 but stimulated by an electric field, and compares host organisms fed with the probiotic strain *Lactobacillus paracasei* (NCM I-2116) (L.p.) in a living state, dead state (dead L.p.), and only the supernatant of the medium (Sn). The control is MRS medium. It can be seen that 21 days after infection the tension of the contraction is clearly reduced in gut muscles from mice that obtained probiotic-derived feeds (live, dead, Sn) if compared to mice fed with MRS only. The values approach the values of uninfected mice.

CONCLUSION

The results lead to the conclusion that probiotics are capable of normalizing the post-infectious hypercontractile state of the bowel muscles. In other words probiotics reduce the sequellae that persist after infection of the gastro-intestinal tract. These effects are different from strain to strain, and in the present experiment, were most substantial with the probiotic strain *Lactobacillus paracasei* (NCM 1-2116) and are present with all *Bifidobacterium* strains that were selected for the experiment.

The overall conclusion from the experiment is that specific probiotic strains, such as *Lactobacillus paracasei* (NCM I-2116), are capable of effecting directly muscle contractility. This general finding has the consequence that, in a general way, gastro-intestinal neuromuscular abnormalities (gut contractions), which are occurring in many instances during an individual's life, may be remedied, treated and/or prevented by administering suitable probiotics.

Abnormal gut contractions occur in babies, infants, adolescents and adults suffering from colic, gut pain or gut discomfort, and such as those described in IBS. Abnormal gut contractions may cause gut invaginations in humans and pets, they may lead to gut distension and to irregular and inappropriate transit time throughout the intestine.

It may be concluded that in these instances, general relief is achieved by administration of probiotics.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method of treating gut pain or gut discomfort related or linked to gut muscular abnormalities comprising the step of administering to a human or an animal having gut pain or gut discomfort an effective amount of a probiotic selected from the group consisting of *Lactobacillus paracasei* CNCM I-2116, *Lactobacillus paracasei* CNCM I-1292, and mixtures thereof, wherein the probiotic is administered in an amount from about $10^6$ to about $10^{14}$ cfu per day.

2. The method according to claim 1, wherein the selected probiotic includes a probiotic selected from the group consisting of dead probiotic bacteria, fermentation substrate and probiotic-derived material.

3. The method according to claim 1, wherein the selected probiotic includes a fermentation substrate of the selected probiotic.

4. The method of claim 1, wherein the composition is a medicament.

5. The method of claim 1, wherein the composition is a nutritional composition.

* * * * *